United States Patent [19]

Seng et al.

[11] B  4,001,324
[45] Jan. 4, 1977

[54] PROCESS FOR PRODUCING N-MONOSUBSTITUTED FORMAMIDES

[75] Inventors: Florin Seng, Schildgen; Kurt Ley, Odenthal-Globusch, both of Germany

[73] Assignee: Bayer Aktiengesellschaft, Leverkusen, Germany

[22] Filed: Oct. 10, 1974

[21] Appl. No.: 513,781

[44] Published under the second Trial Voluntary Protest Program on February 24, 1976 as document No. B 513,781.

[30] Foreign Application Priority Data

Nov. 2, 1973  Germany ............................ 2354717

[52] U.S. Cl. ...................... 260/561 R; 260/562 R
[51] Int. Cl.² ....................................... C07C 103/02
[58] Field of Search .................... 260/561 R, 562 R

[56] References Cited

UNITED STATES PATENTS 3,852,349  12/1974  Turner et al. ................... 260/561 R

*Primary Examiner*—C. Davis
*Attorney, Agent, or Firm*—Burgess, Dinklage & Sprung

[57]  ABSTRACT

An N-monosubstituted formamide having the formula:

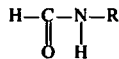

in which R represents an optionally substituted aliphatic, cycloaliphatic or aromatic radical; is prepared by reacting a formaldimine having the formula:

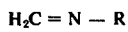

in which R is as defined above; or a hexahydrotriazine having the formula:

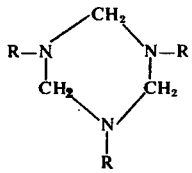

in which R is as defined above, with hydrogen peroxide. The reaction is generally carried out at temperatures in the range of from about 0° to about 100° C.

7 Claims, No Drawings

PROCESS FOR PRODUCING N-MONOSUBSTITUTED FORMAMIDES

This invention relates to a process for the production of N-monosubstituted formamides which comprises reacting formaldimines with hydrogen peroxide.

SUMMARY

It has been found that N-monosubstituted formamides corresponding to the general formula (I):

in which
R represents an optionally substituted aliphatic, cycloaliphatic or aromatic radical, can be obtained by reacting formaldimines corresponding to the general formula (II):

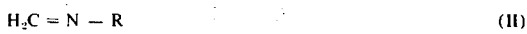

in which R is as defined above, or their trimers, hexahydrotriazines corresponding to the general formula (III):

in which R is as defined above with hydrogen peroxide

DESCRIPTION

The reaction is generally carried out at temperatures in the range of from about 0° to about 100°C, preferably at temperatures in the range of from about 0° to about 50°C and more particularly at temperatures in the range of from 20° to 30°C.

In the context of the invention, optionally substituted aliphatic radicals are linear or branched alkyl radicals with up to 18 carbon atoms, preferably with up to 12 carbon atoms and more especially with up to 6 carbon atoms, such as methyl, ethyl, propyl, isopropyl, butyl, isobutyl, tert.-butyl, amyl, isoamyl and also the isomeric hexyl radicals.

Optionally substituted cycloaliphatic radicals are preferably cycloalkyl radicals containing from 4 to 12 carbon atoms preferably from 4 to 7 carbon atoms, and more especially the cyclopentyl and cyclohexyl radicals.

Optionally substituted aromatic radicals are radicals of the benzene series, more especially the phenyl and naphthyl radicals.

Substituents by which the radicals mentioned above may optionally be substituted include any groups and radicals which are inert with respect to hydrogen peroxide under the reaction conditions under which the process according to the invention is carried out, such as for example the nitro or cyano groups, optionally substituted aryl radicals or alkoxy groups, their alkyl radicals having the scope of meaning defined above.

The radical R may also represent aralkyl, in which case the aromatic portion is preferably phenyl or naphthyl, whilst the aliphatic portion contains preferably up to 8 carbon atoms and more particularly up to 4 carbon atoms; benzyl and phenyl-ethyl are mentioned in particular.

Formaldimines of the general formula (II) and hexahydrotriazines of the general formula (III), which are used as starting compounds in the process according to the invention, are known or can be obtained by known methods (The Chemistry of Heterocyclic Compounds, s-Triazines, 1959, Interscience Publishers INC, New York, pages 473 – 506).

Hydrogen peroxide is known and is commercially available, in particular in the form of an aqueous, approximately 30 to 35 % by weight solution, and also in concentrated form. It is preferably used in standard commercial form because the concentration of the aqueous hydrogen peroxide solution is not critical.

In general, hydrogen peroxide is used in a quantity of at least 1 mol of $H_2O_2$ per mol of formaldimine or per ⅓ mol of hexahydrotriazine. However, it can also be used in an excess of up to 2 mols, more especially up to 1.3 mols of $H_2O_2$ per mol of formaldimine or per ⅓ mol of hexahydrotriazine. It is even possible to use a larger excess of $H_2O_2$.

The reaction according to the invention is generally carried out in an aqueous medium. In this case, the process according to the invention may be carried out as follows:

The formaldimine or hexahydrotriazine used is initially introduced in solution or suspension in water, followed by the addition while cooling of the aqueous hydrogen peroxide solution. The reaction according to the invention is exothermic. In order not to exceed the upper limit of the temperature range selected, the hydrogen peroxide can be added continuously or in portions sufficiently slow such that the temperature range reaction mixture does not exceed that limit through the dissipation of heat. The dissipation of heat can be accelerated with advantage by cooling. After the hydrogen peroxide has been added, the reaction mixture is stirred until the exothermic reaction is complete. The reaction is complete when there is no further increase in the temperature of the reaction mixture or, in the event of external cooling, when the temperature of the reaction mixture falls. In general, the reaction is complete after about 4 to about 10 hours. The N-monosubstituted formamide dissolved in the water may then be isolated from the reaction mixture in the usual way. For example, it may be extracted with a water-immiscible solvent. However, a base, such as an alkali hydroxide or alkali carbonate, may also be added to the reaction mixture in the usual way, and as a result, the N-monosubstituted formamide is precipitated in the form of an oil and may be separated off from the aqueous solution in the usual way.

The reaction may also be carried out in the presence of conventional catalysts (Ullmanns Enzyklopadie der technischen Chemie, 3rd Edition (1962), Vol. 13, page 101), such as osmium tetroxide, vanadium tetroxide, chromium trioxide, molybdenum or tungsten oxides, or the corresponding salts such as tungstates, molybdates (DOS 2,312,373) and uranium salts. The catalyst is generally used in a quantity of from about $10^{-4}$ to about $10^{-1}$ mols and more especially in a quantity of about $10^{-3}$ to about $10^{-2}$ mols per mol of $H_2O_2$ used. Catalysts may be used with particular advantage in cases where the reaction is carried out with aromatically substituted formaldimines or hexahydrotriazines.

In one particular embodiment of the process according to the invention, a water-immiscible solvent may be added to the reaction mixture before the hydrogen peroxide. The reaction according to the invention is then carried out in a two-phase system and, on completion of the reaction, the organic phase containing the reaction product is separated off from the aqueous solution and the N-monosubstituted formamide is subsequently isolated, for example by fractional distillation of the organic phase.

Suitable water-immiscible organic solvents are those which are inert with respect to hydrogen peroxide under the conditions under which the process according to the invention is carried out. Examples of such solvents include aliphatic hydrocarbons and their mixtures of the kind accumulated during the distillation of petroleum, for example petrol; chlorinated aliphatic hydrocarbons such as methylene chloride and carbon tetrachloride; and aromatic hydrocarbons such as benzene, toluene or xylene.

The reaction according to the invention is illustrated by the following equation which relates by way of example to tert.-butylformaldimine:

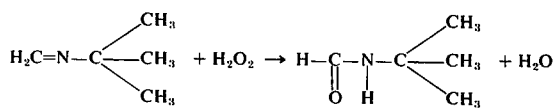

In another advantageous embodiment of the process according to the invention, the formaldimine of formula (II) or hexahydrotriazine of formula (III) used as starting compound is not isolated after its preparation, but is instead subsequently directly reacted with hydrogen peroxide by the process according to the invention in the same reaction vessel. To this end, the amine corresponding to the formaldimine or hexahydrotriazine used may be combined with formaldehyde, optionally in aqueous solution, in a stoichiometric ratio and, on completion of this reaction, the reaction with hydrogen peroxide according to the invention is subsequently carried out in the same way as described above using this reaction mixture as the starting solution.

The advantages of the process according to the invention include in particular the fact that the starting compounds used are readily obtainable, the fact that the process can readily be carried out and the high yields obtained.

N-monosubstituted formamides may be used as solvents or as intermediate products, for example, for the production of isonitriles (L. Ugi, Angew. Chem: 77, 492 (1965).

EXAMPLE 1

8.5 g (0.1 mol) of N-tert.-butyl formaldimine are introduced into 30 ml of water, followed by the dropwise addition of 11.5 g (0.1 mol) of a 30 % by weight aqueous hydrogen peroxide solution. The temperature is kept between 20° and 30°C by occasional cooling. The reaction is complete after about 4 hours. 50 g of concentrated (40 % by weight) aqueous sodium hydroxide solution are then added to the mixture with thorough cooling. The N-tert.-butylformamide is precipitated in the form of a colourless oil. It is extracted with cyclohexane and, after drying over sodium sulphate, the organic phase is subjected to fractional distillation in vacuo, giving 9 g (89 % of the theoretical yield) of N-tert.-butylformamide boiling at 82° to 84°C/14 Torr.

EXAMPLE 2

25.5 g (0.3 mol) of 1,3,5,-tri-n-butylhexahydrotriazine are dissolved in 30 ml of water, followed by the dropwise addition of 34.5 g (0.1 mol) of 30 % by weight aqueous hydrogen peroxide solution. The temperature is kept between 20° and 30°C by occasional cooling. The reaction is complete after about 4 hours. 50 g of concentrated (40 % by weight) aqueous sodium hydroxide solution are then added to the reaction mixture with thorough cooling. The N-n-butylformamide is precipitated in the form of a colourless oil. It is extracted with cyclohexane and the organic phase is subjected to fractional distillation in vacuo after drying over sodium sulphate. N-n-butylformamide boiling at 120°C/10 Torr is obtained in a yield of 22 g or 72 % of the theoretical amount.

EXAMPLE 3

25.5 g (0.1 mol) of N-triisobutyl-1,3,5-hexahydrotriazine are dissolved in 30 ml of water, followed by the dropwise addition of 34.5 g (0.3 mol) of 30 % by weight aqueous hydrogen peroxide solution. The temperature is kept between 20° and 30°C by occasional cooling. The reaction is over after about 4 hours. 50 g of concentrated (40 % by weight) aqueous sodium hydroxide solution are then added to the reaction mixture with thorough cooling. The N-isobutylformamide is precipitated in the form of a colourless oil. It is taken up in cyclohexane and separated off from the aqueous phase. The aqueous phase is repeatedly extracted with small quantities of cyclohexane. The organic phases are combined, dried over sodium sulphate and subsequently subjected to fractional distillation in vacuo giving 25 g (82 % of the theoretical yield) of N-isobutylformamide boiling at 115°C/10 Torr.

EXAMPLE 4

22 g (0.1 mol) of N-tri-n-propyl-1,3,5-hexahydrotriazine are dissolved in 30 ml of water, followed by the dropwise addition of 34.5 g (0.3 mol) of 30 % by weight aqueous hydrogen peroxide solution. The temperature is kept between 20° and 30°C by occasional cooling. The reaction is over after about 4 hours. 50 g of concentrated (40 % by weight) aqueous sodium hydroxide solution are then added to the mixture with thorough cooling. The N-n-propylformamide is precipitated in the form of a colourless oil. It is taken up with methylene chloride and separated off. The aqueous phase is repeatedly extracted with methylene chloride. The combined organic phases are dried over sodium sulphate and subsequently subjected to fractional distillation in vacuo, giving 20 g (76 % of the theoretical yield) of N-n-propylformamide boiling at 87°C/10 Torr.

EXAMPLE 5

22 g (0.1 mol) of N-triisopropyl-1,3,5-hexahydrotriazine are dissolved in 30 ml of water, followed by the dropwise addition of 34.5 g (0.3 mol) of 30 % by weight aqueous hydrogen peroxide solution. The temperature is kept between 20° and 30°C by occasional cooling. The reaction is over after about 4 hours. 50 g of concentrated (40 % by weight) aqueous sodium hydroxide solution are then added to the mixture with thorough cooling. The N-isopropylformamide is precipitated in the form of a colourless oil. It is taken up with methylene chloride and separated off. The aqueous phase is repeatedly extracted with methylene chloride. The combined organic phases are dried over sodium sulphate and subsequently subjected to fractional distillation in vacuo, giving 21 g (81 % of the theoretical yield) of N-isopropylformamide boiling at 105°C/12 Torr.

EXAMPLE 6

46 g (0.4 mol) of a 30 % by weight aqueous hydrogen peroxide solution are added dropwise with stirring to 12.9 g (0.1 mol) of N-trimethyl-1,3,5-hexahydrotriazine in a mixture of 30 ml of water and 30 ml of methylene chloride. The temperature is prevented from exceeding 50°C by occasional cooling. On completion of the addition, which takes about 4 hours, the reaction mixture is left standing for a further 12 hours, after which the methylene chloride phase is separated off. The aqueous phase is then extracted twice by shaking with 50 ml of methylene chloride. The combined organic phases are dried over sodium sulphate and subjected to fractional distillation in a water jet vacuum, giving 8.5 g (48 % of the theoretical yield) of N-methylformamide boiling at 80°C/14 Torr.

EXAMPLE 7

46 g (0.4 mol) of a 30 % by weight aqueous hydrogen peroxide solution are added dropwise with stirring to 17.1 g (0.1 mol) of tri-N-ethyl-1,3,5-hexahydrotriazine in a mixture of 30 ml of water and 30 ml of methylene chloride. The temperature is prevented from exceeding 50°C by occasional cooling. The addition is completed after about 4 hours and the reaction mixture is left standing for a further 12 hours. The methylene chloride phase is then separated off and the aqueous phase is extracted twice by shaking with 50 ml of methylene chloride. The combined organic phases are dried over sodium sulphate and subjected to fractional distillation in a water-jet vacuum, giving 11.4 g (52 % of the theoretical yield) of N-ethyl-formamide boiling at 95°C/17 Torr.

EXAMPLE 8

46 g (0.4 mol) of a 30 % by weight aqueous hydrogen peroxide solution are added dropwise with stirring to 26.1 g (0.1 mol) of tri-(N-2-methoxyethyl)-1,3,5-hexahydrotriazine in a mixture of 30 ml of water and 30 ml of methylene chloride. The temperature is prevented from exceeding 50°C by occasional cooling. The reaction mixture is then stirred for another 4 hours, and subsequently left standing for 12 hours. The methylene chloride phase is then separated off and the aqueous phase extracted twice by shaking with 50 ml of methylene chloride. The combined organic phases are dried over sodium sulphate and subjected to fractional distillation in a water jet vacuum, giving 17.8 g (58 % of the theoretical yield) of N-2-methoxyethylformamide boiling at 120° to 126°C/19 Torr.

EXAMPLE 9

30 g (0.3 mol) of cyclohexylamine are dissolved in 80 ml of water, followed by the dropwise addition of 30 g (0.3 mol) of a 30 % by weight aqueous formaldehyde solution. The white precipitate of tri-(N-cyclohexyl)-1,3,5-hexahydrotriazine is dissolved by the addition of 30 ml of methylene chloride.

46 g (0.4 mol) of a 30 % by weight aqueous hydrogen peroxide solution are added with stirring to this solution of tri-(N-cyclohexyl)-1,3,5-hexahydrotriazine. The temperature is prevented from exceeding 50°C by occasional cooling. The reaction mixture is then stirred for another 10 hours during which the temperature is kept below 50°C by occasional cooling. The organic phase is then separated off and the aqueous phase is extracted twice by shaking with 50 ml of methylene chloride. The combined organic phases are dried over sodium sulphate and subsequently subjected to fractional distillation, giving 29 g (76 % of the theoretical yield) of N-cyclohexylformamide boiling at 145° to 149°C/17 Torr.

EXAMPLE 10

32.1 g (0.3 mol) of benzylamine are dissolved in 30 ml of water, followed by the dropwise addition of 30 g (0.3 mol) of a 30 % by weight aqueous formaldehyde solution. The white precipitate of tri-(N-benzyl)-1,3,5-hexahydrotriazine is dissolved by the addition of 30 ml of methylene chloride.

46 g (0.4 mol) of a 30 % by weight aqueous hydrogen peroxide solution are then added with stirring, the temperature being kept below 30°C by occasional cooling. The reaction mixture is then stirred for another 10 hours during which the temperature is kept below 30°C. The organic phase is then separated off and the aqueous phase extracted twice by shaking with 50 ml of methylene chloride. The combined organic phases are dried over sodium sulphate and subsequently subjected to fractional distillation, giving 27 g (72 % of the theoretical yield) of N-benzylformamide boiling at 159° to 163°C/18 Torr.

EXAMPLE 11

18.6 g (0.2 mol) of aniline are introduced into 30 ml of water, followed by the dropwise addition with stirring of 20 g (0.2 mol) of a 30 % by weight aqueous formaldehyde solution. 0.2 g of sodium tungstate are then added, followed by the dropwise addition with continued stirring of 25 g of a 30 % by weight aqueous hydrogen peroxide solution. The temperature rises to about 60° to 70°C. The dark oil precipitated is taken up in about 30 ml of methylene chloride and the organic phase is separated off. The aqueous phase is repeatedly extracted with methylene chloride. The combined organic phases are dried over sodium sulphate and subsequently subjected to fractional distillation in vacuo, giving 12.2 g (51 % of the theoretical yield) of formanilide boiling at 160° to 172°C/ 15 Torr.

What is claimed is:
1. Process for producing an N-monosubstituted formamide having the formula:

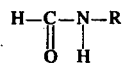

in which R is selected from the group of linear and branched alkyl having up to 18 carbon atoms, cycloalkyl having 4 to 12 carbon atoms, phenyl and naphthyl, the foregoing substituted by nitro, cyano, aryl or alkoxy, and aralkyl wherein the aromatic portion is phenyl or naphthyl and the alkyl portion has up to 8 carbon atoms;

which comprises reacting a formaldimine having the formula:

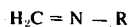

in which R is as defined above; or a hexahydrotriazine having the formula

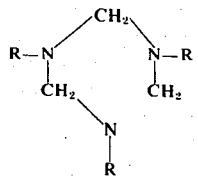

in which R is as defined above, with hydrogen peroxide.

2. Process as claimed in claim 1 wherein the reaction is carried out in an aqueous medium.

3. Process as claimed in claim 1 wherein the reaction is carried out at a temperature in the range of from 0° to 100°C.

4. Process as claimed in claim 1 wherein the reaction is carried out at a temperature in the range of from 0° to 50°C.

5. Process as claimed in claim 1 wherein the reaction is carried out at a temperature of from 20° to 30°C.

6. Process as claimed in claim 1 wherein the reaction is carried out in a two-phase system comprising water and a water-immiscible solvent.

7. Process as claimed in claim 1 wherein the formaldimine or hexahydrotriazine is reacted with hydrogen peroxide immediately after its preparation without intermediate isolation.

* * * * *

UNITED STATES PATENT AND TRADEMARK OFFICE
CERTIFICATE OF CORRECTION

PATENT NO. : 4,001,324
DATED : 1/4/77
INVENTOR(S) : Florin Seng et al

It is certified that error appears in the above-identified patent and that said Letters Patent are hereby corrected as shown below:

Column 1, line 13 - In the formula $\underset{\underset{O}{\parallel}}{G}$ should read $\underset{\underset{O}{\parallel}}{C}$ Column 7, line 12 - Bond omitted in formula between bottom $\underset{R}{\overset{}{N}}$ and $CH_2$ Signed and Sealed this Nineteenth Day of April 1977

[SEAL]

Attest:

RUTH C. MASON
*Attesting Officer*

C. MARSHALL DANN
*Commissioner of Patents and Trademarks*